(12) United States Patent
Chen et al.

(10) Patent No.: US 10,362,786 B2
(45) Date of Patent: *Jul. 30, 2019

(54) STABLE AQUEOUS SPORE-CONTAINING FORMULATION

(75) Inventors: Chi-Yu Roy Chen, Raleigh, NC (US); Kevin Bugg, Raleigh, NC (US); Jennifer Riggs, Raleigh, NC (US)

(73) Assignee: Bayer Intellectual Property GMBH, Monheim am Rhein (DE)

( * ) Notice: Subject to any disclaimer, the term of this patent is extended or adjusted under 35 U.S.C. 154(b) by 307 days.

This patent is subject to a terminal disclaimer.

(21) Appl. No.: 12/867,149

(22) PCT Filed: Mar. 31, 2009

(86) PCT No.: PCT/US2009/038861
§ 371 (c)(1),
(2), (4) Date: Oct. 27, 2010

(87) PCT Pub. No.: WO2009/126473
PCT Pub. Date: Oct. 15, 2009

(65) Prior Publication Data
US 2011/0033436 A1  Feb. 10, 2011

Related U.S. Application Data

(60) Provisional application No. 61/123,278, filed on Apr. 7, 2008.

(51) Int. Cl.
*A01N 63/00* (2006.01)
*A01N 63/04* (2006.01)
*A01N 25/02* (2006.01)
*A01N 25/04* (2006.01)

(52) U.S. Cl.
CPC .............. *A01N 63/00* (2013.01); *A01N 63/04* (2013.01)

(58) Field of Classification Search
None
See application file for complete search history.

(56) References Cited

U.S. PATENT DOCUMENTS

| 4,487,687 A | 12/1984 | Simo et al. |
| 5,019,389 A | 5/1991 | Riggs et al. |
| 5,041,290 A | 8/1991 | Gindrat et al. |
| 5,215,747 A | 6/1993 | Hairston et al. |
| 5,474,971 A | 12/1995 | Sandell |
| 5,512,279 A | 4/1996 | Jarrett et al. |
| 5,707,551 A | 1/1998 | Pallas et al. |
| 5,730,973 A * | 3/1998 | Morales ............... A01N 63/00 424/405 |
| 5,795,845 A | 8/1998 | Yang et al. |
| 6,168,947 B1 | 1/2001 | Tzean et al. |
| 6,232,270 B1 * | 5/2001 | Branly et al. ............ 504/117 |
| 6,406,690 B1 * | 6/2002 | Peleg et al. ............ 424/93.46 |
| 6,471,741 B1 | 10/2002 | Reinbergen |
| 6,582,712 B2 | 6/2003 | Pullen |
| 6,753,296 B1 | 6/2004 | Senn et al. |
| 7,718,572 B2 * | 5/2010 | Igari et al. ............ 504/359 |
| 8,039,006 B2 * | 10/2011 | Prato ............ 424/246.1 |
| 2003/0125212 A1 * | 7/2003 | Yamaguchi ........ A01N 25/30 504/365 |
| 2005/0208144 A1 | 9/2005 | Igari et al. |
| 2006/0013846 A1 * | 1/2006 | Kurita et al. ............ 424/405 |
| 2006/0193882 A1 | 8/2006 | Botts et al. |
| 2007/0093387 A1 | 4/2007 | Sumi et al. |
| 2011/0110906 A1 | 5/2011 | Andersch et al. |

FOREIGN PATENT DOCUMENTS

| CA | 965001 | 3/1975 |
| CA | 2146822 A1 | 10/1995 |
| DE | 2250085 A1 | 4/1973 |
| EP | 0 677 247 A1 | 10/1995 |
| EP | 0556238 | 1/1997 |
| WO | 9510597 | 4/1995 |
| WO | 98/23157 A1 | 6/1998 |
| WO | 2007149817 | 12/2007 |

OTHER PUBLICATIONS

Yandoc et al., Weed Technology. 2005. vol. 19:19-26.*
Powell., (Journal of General Microbiology, vol. 4, No. 3, pp. 330-339.*
Murrell et al., Journal of Bacteriology, Nov. 1977, vol. 129, No. 3, p. 1272-1280).*
Vary., Journal of Bacteriology, Nov. 1973, vol. 116, No. 2p. 797-802.*
Cerf et al., Ann Microbiol (Paris). Jan. 1975;126(1):23-38.*
Translation of Cerf et al., Ann Microbiol (Paris). Jan. 1975;126(1):23-38.*
Garcia et al., Journal of Applied Bacteriology, 1989, vol. 67, pp. 619-628.*
Harnulv et al., Journal of Applied Bacteriology, 1972, vol. 35, pp. 616-624.*
Allured, Michael, McCutcheon's, vol. 1: Emulsifiers and Detergents, 2002, pp. 291-312, McCutcheon's Publishing Company, Glen Rock, NJ, US.
Chen, Z. X. et al., ed.; Nematology: Advances and Perspectives, vol. 2: Nematode Management and Utilization, 2004, pp. 979-1039, Cabi Publishing, Cambridge, MA, US.

(Continued)

*Primary Examiner* — Emily A Cordas

(57) ABSTRACT

Stable aqueous spore-containing chemical formulations having a low to medium viscosity profile are provided. The formulations comprise at least one spore in a mixture of water and at least one water miscible solvent, optionally at least one surfactant, optionally at least one stabilizer such as a metal salt, optionally at least one biocide, optionally at least one buffer, and optionally at least one chemical insecticide or fungicide or a mixture thereof. The formulations are particularly suitable as a seed coating and foliar spray. Methods of preparation as well as methods of treating a plant are also provided.

23 Claims, No Drawings

(56) References Cited

OTHER PUBLICATIONS

Chen, Z. X. et al., ed.; Nematology: Advances and Perspectives, vol. 2: Nematode Management and Utilization, 2004, pp. 1041-1082, Cabi Publishing, Cambridge, MA, US.
Colby, S. R., Calculating Synergistic and Antagonistic Responses of Herbicide Combinations, Weeds, vol. 15, No. 1, Jan. 1967, pp. 20-22, Weed Science of America and Allen Press.
MeisterPro Crop Protection Handbook, 2006, pp. F21-F22, Meister Media Worldwide, Willoughby, OH, US.
The Merck Index, An Encyclopedia of Chemicals, Drugs, and Biologicals, Eleventh Edition, 1989, pp. MICS63-MICS65, Merck & Co., Inc., Rahway, NJ, US.
Todar, Kenneth PhD, Todar's Online Textbook of Bacteriology, *Staphylococcus epidermidis*, www.textbookofbacteriology.net/index.html.
Extended European search report for PCT/US2009/038861.
International Search Report for PCT/US09/38861, Filed Mar. 31, 2009.
Supplementary European Search Report for PCT/US2009/038861.
J. DeAngelis, "Natural/Organic Dust Insecticides," livingwithbugs.com/use_dust.html, (2004) accessed on Jun. 2, 2015, 2 pages.
National Library of Medicine, "Distillates (petroleum), hydrotreated heavy naphthenic, RN: 64742-52-5" chem.sis.nlm.nih.gov/chemidplus/rn/64742-52-5, (2008) accessed on Jun. 2, 2015, 4 pages.
National Library of Medicine, "Distillates (petroleum), hydrotreated light naphthenic RN: 64742-53-6" chem.sis.nlm.nih.gov/chemidplus/rn/64742-53-6, (2008) accessed on Jun. 2, 2015, 2 pages.
Office Action dated Apr. 26, 2013 in U.S. Appl. No. 12/936,700, Andersch, W. et al., filed Jan. 3, 2011, United States Patent and Trademark Office.
Office Action dated Nov. 12, 2013 in U.S. Appl. No. 12/936,700, Andersch, W. et al., filed Jan. 3, 2011, United States Patent and Trademark Office.
Environmental Protection Agency: Pesticide Products; Registration Application—Bacillus firmus strain I-1582, Federal Register, vol. 72, No. 44, Mar. 7, 2007 (Mar. 7, 2007), pp. 10210-10211.

\* cited by examiner

STABLE AQUEOUS SPORE-CONTAINING FORMULATION

CROSS REFERENCE TO RELATED APPLICATIONS

This application is a 371 National-Stage Application of PCT/US09/38861, filed Mar. 31, 2009, which claims the benefit of U.S. Provisional Application No. 61/123,278, filed Apr. 7, 2008, the contents of each of which are herein incorporated by reference in their entireties.

BACKGROUND OF THE INVENTION

Field of the Invention

The present invention relates generally to agricultural liquid formulations. More specifically, the present invention relates to agriculturally acceptable, stable aqueous spore-formulations and spore and chemical combination formulations, their methods of preparation as well as methods of treating a plant.

Description of Related Art

Spores of both bacterial and fungal origin have been used commercially as bio-insecticides and bio-fungicides or bio-control agents (BCA). They are typically used as part of an integrated pest management (1PM) program, and most formulations have been either in powder or liquid form. Markets such as foliage sprays, for example Bt (*Bacillus thuringiensis*), and soil drench sprays, when combined with fertilizer or as ingredient of seed treatment products have proven to be useful in many cases. The advantages of BCA products are their environmental friendliness and safety towards users and non-target crops or beneficial insects. However, some, if not all straight spore BCA type of products has suffered from poor efficacy or control in the field. One possible solution to the problem was to combine the spore BCA with chemical control agents such as insecticides or fungicides. Another difficult aspect of the liquid formulation is the stability or viability of the spores over extended time, especially in aqueous liquid formulations. A solution to the stability problem has been demonstrated in a low concentration aqueous liquid formulations (U.S. Pat. No. 6,471,741). See also U.S. Pat. Nos. 5,707,551 and 6,232,270 for nonaqueous suspension concentrates or agricultural composition containing bacteria, respectively.

Agriculturally acceptable formulations containing both spores and chemicals of various types are commercially available in the form of powders (i.e., dry formulations). Such powders include wettable powders or water dispersible granules. Dry formulations containing both spores and chemicals have historically been preferred over liquid formulations because dry formulations inherently provide a more stable environment for spores and dry spores are easily combined with various chemicals within such dry formulations. Liquid formulations, however, exhibit a distinct advantage over dry formulations in terms of ease and breadth of agricultural application. Liquid formulations can also provide a more uniform seed treatment.

U.S. Pat. No. 5,215,747 discloses a storage stable pre-mix composition containing *Bacillus subtilis* endospores and at least one chemical fungicide component. The formulations disclosed therein include powder, granular and liquid formulations. The liquid formulations, however, contain organic solvents such as xylene, methanol or ethylene glycol which in some circumstances can be phytotoxic to the spore. As such, aqueous formulations of spores and chemicals should offer a desirable alternative to the liquid formulations disclosed in U.S. Pat. No. 5,215,747.

Maintaining storage stability is a unique challenge for aqueous, liquid formulations containing both spores, such as bacterial spores, and chemicals such as agriculturally useful chemicals such as pesticides, herbicides, fungicides and the like. Typically, a spore-containing product such as a pesticide must maintain a shelf life of one to two years at a minimum. However, an aqueous media inherently facilitates premature germination of the spores before application. To date, such germination and stability issues have been circumvented by diluting dry spore-containing formulations with water just before application (i.e., drench or dip applications) which presents additional cost and reduced efficiency for the grower.

Yet another challenge associated with aqueous spore-containing formulations is that of increased formulation viscosity upon mixture of the spores and the chemicals. Spores exhibit an enhanced tendency to yield high viscosity formulations because spores inherently absorb water resulting a substantial increase in overall spore volume compared to a spore in a dehydrated state. A high viscosity profile formulation poses challenging mixing and application problems for the farmer or seed treater.

SUMMARY OF THE INVENTION

The present invention provides a low to medium viscosity agriculturally acceptable, stable aqueous spore as well as a spore-containing formulation. In accordance with the present invention there is provided an agriculturally acceptable stable aqueous formulation comprising (i) at least one spore preferably present in an amount of from 3% w/w to 80% w/w, (ii) a water miscible solvent or an aqueous emulsion of a hydrophobic agent, preferably in an amount of 5 to 90% w/w, and (iii) water in sufficient amount to bring the total to 100% w/w. The formulation can include other components such as optionally at least one surfactant, optionally at least one dispersant, optionally at least one stabilizer such as a alkaline metal or alkaline earth metal or salt of aluminium, ammonium, iron and/or zinc, optionally at least one biocide, optionally at least one buffer, and optionally at least one agriculturally useful chemical including but not limited to one or more pesticides, fungicides and the like. Pesticides include but are not limited to insect ides.

Methods of preparing an agriculturally acceptable stable aqueous spore and spore-containing formulation are also provided. The present methods of preparation preferably utilize a high loading spore suspension or slurry (module), optionally in combination with a highly concentrated chemical formulation or mill base (module) that is separately prepared. The resultant spore formulation is mixed under mild agitation resulting in a reasonable viscosity profile for ease of application by farmers and seed treaters.

Methods of protecting a plant are also provided. The present formulations may be applied in any desired manner, such as in the form of a seed coating, soil drench and/or directly in-furrow, and/or as a foliar spray, and applied either pre-mergence, post-emergence or both, and the like. In other words, the composition can be applied to the seed, the plant or to the fruit of the plant or to the soil wherein the plant is growing or wherein it is desired to grow.

The foregoing and other aspects of the present invention are explained in detail in the detailed description set forth below.

DETAILED DESCRIPTION OF A PREFERRED EMBODIMENT

It is an object of the present invention to provide an agriculturally acceptable stable aqueous formulation comprising (a) at least one spore present in an amount of from 3% w/w to 80% w/w, (b) a water miscible solvent and/or an aqueous emulsion of a hydrophobic agent, in an amount of 2 to 90% w/w, and (c) balance water.

It is a further object of the present invention to provide such an agriculturally acceptable stable aqueous formulation wherein the at least one spore is selected from the group consisting of a bacterial species, a fungal species, and combinations thereof.

It is a further object of the present invention to provide such an agriculturally acceptable stable aqueous formulation wherein the bacterial species spore is from the Genus *Bacillus*.

It is a further object of the present invention to provide such an agriculturally acceptable stable aqueous formulation wherein the bacterial species spore is at least one from *Bacillus aizawai, Bacillus cereus, Bacillus firmus, Bacillus kurstaki, Bacillus lentimorbus, Bacillus licheniformis, Bacillus megaterium, Bacillus popillae, Bacillus pumilus, Bacillus sphaericus, Bacillus subtilis*, and/or *Bacillus thuringiensis*, and is preferably *Bacillus firmus* of strain CNCM I-1582.

It is a further object of the present invention to provide such an agriculturally acceptable stable aqueous formulation wherein the fungal species spore is from the Class of Basidiomycetes, Chytridiomycetes, Deuteromycetes, Hyphochytridiomycetes, Oomycetes, Plasmodiophoromycetes, Sordariomycetes, Trichomycetes and Zygomycetes.

It is a further object of the present invention to provide such an agriculturally acceptable stable aqueous formulation wherein the fungal species spore is at least one from *Arthrobotrys superba, Arthrobotrys irregular, Beauveria bassiana, Fusarium* spp., *Hirsutella rhossiliensis, Hirsutella thompsonii, Lagenidium giganteum, Myrothecium, Nomuraea rileyi, Paecilomyces lilacinus, Trichoderma, Vericillium lecanii*, and/or *Verticillium lecanii*.

It is a further object of the present invention to provide such an agriculturally acceptable stable aqueous formulation wherein the at least one water miscible solvent is a polar, organic solvent.

It is a further object of the present invention to provide such an agriculturally acceptable stable aqueous formulation wherein the polar water miscible organic solvent comprises 1, 3 butylene glycol, 2-pyrrolidone, acetone, acetonitrile, an aliphatic alcohol, an aliphatic carboxylic acid alkyl ester, cyclohexanone, di- and triglycols, diacetone alcohol, dialkyl ketone, diethylene glycol, diglyme, DMF, DMSO, ethanol, ethyl acetate, formamide, furfuryl alcohol, gamma-butyrolactone, glycerol, glycofurol, a glycol ether, glycol, hexamethylene glycol, isopropanol, methyl ethyl ketone, N-methyl pyrrolidone, pentamethylene glycol, phosphoric acid esters, polyethylene glycol, polyethylene glycols, polyhydroxylated alkanes, propanol, propylene carbonate, propylene glycol, pyrrolidine, pyrrolidine, sulfolane, tetrahydrofuran, tetramethylene glycol, thiodiglycol, and/or triethylene glycol and combinations thereof.

It is a further object of the present invention to provide such an agriculturally acceptable stable aqueous formulation wherein the at least one hydrophobic agent is: (a) a hydrogenated heavy naphthenic distillate; (b) a hydrogenated vegetable oil; and/or (c) a plant sourced oil, including but not limited to almond oil, canola oil, coconut oil, corn oil, cottonseed oil, flaxseed oil, grape seed oil, jojoba oil, linseed oil, mustard oil, olive oil, palm oil, peanut oil, rapeseed oil, rice bran oil, safflower oil, sesame oil, soybean oil, sunflower oil, and walnut oil and mixtures thereof.

It is a further object of the present invention to provide such an agriculturally acceptable stable aqueous formulation further comprising at least one chemical, wherein the at least one chemical is at least one selected from the group consisting of a surfactant, a dispersant, a suspension aid, a stabilizer, a biocide, a buffer, an insect control agent, a pesticide, a fungicide and combinations thereof.

It is a further object of the present invention to provide such an agriculturally acceptable stable aqueous formulation wherein, (a) the surfactant is selected from the group consisting of a nonionic surfactant, an anionic surfactant and combinations thereof; (b) the dispersant is selected from the group consisting of an ionic water soluble polymer, an anionic water soluble polymer and combinations thereof, wherein (i) the ionic water soluble polymer is selected from the group consisting of lignin sulfonate dispersant, polyacrylate, or a sodium salt of said polyacrylate or combination thereof; and (ii) the nonionic water soluble polymer is a vinyl pyrrolidone homopolymer or copolymer, or poly (vinyl alcohol) and/or poly(ethylene oxide), or mixtures thereof; (c) the suspension aid is selected from the group consisting of xanthan gum, hydroxypropyl cellulose, ethyl cellulose, vinyl pyrrolidone homo- and co-polymers, polyacrylic acid, sodium polyacrylate, hydroxyethyl cellulose, carboxyl methyl cellulose, guar gum, starch, derivatized guar and polyacrylamide, attapulgite, montmorillonite, organically modified montmorillonite clays, alumina, and/or precipitated silica and combinations thereof; (d) the stabilizer is at least one chemical salt compound having (i) at least one cation selected from the group consisting of aluminum, calcium, copper, iron, magnesium, potassium, sodium, and zinc, and (ii) at least one anion selected from the group consisting of acetates, bromides, carbonates, chlorides, chlorites, chromates, citrates, condensed phosphates, cyanates, dihydrogen phosphates, dihydrogen phosphates, fluorides, formates, hydrogen carbonates, bicarbonates, hydrogen phosphate, hydrogen phosphites, hydrogen sulfites, hydrogen bisulfites, hypochlorites, hypophosphites, nitrates, nitrites, orthophosphates, oxalates, phosphates, phosphides, phosphonates, pyrophosphates, salicylates, silicates, sulfates, sulfides, sulfites, thiocyanates, and thiosulfates, wherein the stabilizer is preferably sodium sulfate, sodium chloride, potassium chloride or zinc sulfate; (e) the biocide is selected from the group consisting of 5-chloro-2-methyl-3(2H)-isothiazolone (e.g., trade name, Kathon), o-phenylphenol, sodium o-phenylphenate, cis-1-(chloroallyl)-3,5,7-triaza-1-azoniaadamantane chloride, 7-ethyl bicyclooxazolidine, 2,2-dibromo-3-nitrilopropionamide, bronopol, glutaraldehyde, copper hydroxide, cresol, dichlorophen, dipyrithione, dodidin, fenaminosulf, formaldehyde, hydrargaphen, 8-hydroxyquinoline sulfate, kasugamycin, nitrapyrin, octhilinone, oxolinic acid, oxytetracycline, probenazole, streptomycin, tecloftalam, thimerosal, polyquaternary ammonium chloride, alkylbenzyl dimethyl ammonium chloride, 2-methyl-4-isothiazolone, 2-ethyl-4-isothiazolin-3-one, 2-propyl-4-isothiazolin-3-one, 2-butyl-4-isothiazolin-3-one, 2-amyl-4-isothiazolin-3-one, 5-chloro-2-methyl-4-isothiazolin-3-one, 5-bromo-2-methyl-4-isothiazolin-3-one, 5-iodo-2-methyl-4-isothiazolin-3-one, 5-chloro-2-butyl-4-isothiazolin-3-one, 5-bromo-2-ethyl-4-isothiazolin-3-one, 5-iodo-2-amyl-4-isothiazolin-3-one, 2-n-octyl-4-isothiazolin-3-one, and 4,5-dichloro-2-n-octyl-4-isothiazolin-3-one, 1,2-benzisothiazolin-3-one, and combinations thereof; (f) the buffer is selected from the group consisting of citric acid, ascorbic acid, hydrochloric acid, sulfuric acid and combinations thereof; (g) the insect control agent is selected from the group consisting of 1-(6-chloro-3-pyridylmethyl)-N-nitroimidazolidin-2-ylideneamine (imidacloprid), 3-(6-chloro-3-pyridylmethyl)-1,3-thiazolidin-2-ylidenecyanamide (thiacloprid), 1-(2-chloro-1,3-thiazol-5-ylmethyl)-3-methyl-2-nitroguanidine (clothianidin), nitempyran, $N^1$-[(6-chloro-3-pyridyl)methyl]-$N^2$-cyano-$N^1$-methylacetamidine (acetamiprid), 3-(2-chloro-1,3-thiazol-5-ylmethyl)-5-methyl-1,3,5-oxadiazinan-4-ylidene(nitro) amine (thiamethoxam), 1-methyl-2-nitro-3-(tetrahydro-3-furylmethyl)guanidine (dinotefuran) and carbamates including but not limited to aldicarb, carbaryl, carbofuran and thiodicarb, and combinations thereof; and (h) the fungicide is selected from the group consisting of acibenzolar-S-methyl, azoxystrobin, benalaxyl, benalaxyl-M, benomyl, benthiavalicarb-isopropyl, bitertanol, blasticidin-S, boscalid, bromuconazole, captafol, captan, carbendazim, carboxin, carpropamide, chlorothalonil, fungicidal compositions based on copper, derivatives of copper such as copper hydroxide and copper oxychloride, cyazofamide, cylfufenamid, cymoxanil, cyproconazole, cyprodinil, dichloran, diclocymet, diethofencarb, difenoconazole, diflumetorim, dimethomorph, diniconazole, discostrobin, dodemorph, dodine, edifenphos, epoxyconazole, ethaboxam, ethirimol, famoxadone, fenamidone, fenarimol, fenbuconazole, fenhexamide, fenpiclonil, fenpropidine, fenpropimorph, ferimzone, fluazinam, fludioxonil, flumetover, fluopicolide, fluoxastrobin, fluquinconazole, flusilazole, flusulphamide, flutolanil, flutriafol, folpel, fosetyl-Al, furalaxyl, furametpyr, guazatine, hexaconazole, hymexazol, imazalil, ipconazole, iprobenphos, iprodione, iprovalicarb, isoprothiolane, kasugamycin, kresoxim-methyl, mancozeb, mandipropamid, maneb, mefenoxam, mepanipyrim, metalaxyl and their enantiomeric forms such as metalaxyl-M, metconazole, metiram-zinc, metominostrobin, oxadixyl, metrafenone, orysastrobin, pefurazoate, penconazole, pencycuron, penthiopyrad, phtalide, picoxystrobin, probenazole, prochloraz, procymidone, propamocarb, propiconazole, proquinazid, prothioconazole, pyraclostrobin, pyrimethanil, pyroquilon, quinoxyfen, silthiofam, simeconazole, spiroxamine, tebuconazole, tetraconazole, thiabendazole, thifluzamide, thiophanate, thiophanate-methyl, thiram, tolyfluanid, triadimefon, triadimenol, tricyclazole, tridemorph, trifloxystrobin, triticonazole, derivatives of valinamide such as for example, iprovalicarb, vinclozolin, zineb, zoxamide, and combinations thereof.

It is a further object of the present invention to provide such an agriculturally acceptable stable aqueous formulation wherein the chemical is selected from one or more of the group consisting of: (a) a surfactant comprising from 0.2% w/w to 50% w/w of at least one nonionic surfactant and/or from 0.1% w/w to 25% w/w of at least one anionic surfactant, and combinations thereof; (b) from 0.1% w/w to 37% w/w of said dispersant; (c) from 0.5% w/w to 25% w/w of said suspension aid; (d) from 0.5% w/w to 30% w/w of said stabilizer; (e) from 0.1% w/w to 12% w/w of said biocide; (f) from 0.1% w/w to 3% w/w of said buffer; (g) from 1% w/w to 99% w/w of said insect control agent; (h) from 1% w/w/to 60% w/w of said fungicide; and (i) water in a sufficient amount to bring to 100% w/w.

It is a further object of the present invention to provide such an agriculturally acceptable stable aqueous formulation that exhibits a viscosity between 150 to 3500 cps by Brookfield viscometry and a pH of about 2.5 to 9.5.

The present invention is also directed to providing a method of protecting a plant comprising: (a) providing an aqueous formulation, the formulation comprising at least one spore in an amount of from 3% w/w to 80% w/w; at least one water miscible solvent and/or an aqueous emulsion of a hydrophobic agent in an amount of 5% w/w to 50% w/w, from 1% w/w to 60% w/w of an insect control agent, pesticide and/or fungicide, optionally, from 0.2% w/w to 20% w/w of at least one nonionic surfactant; optionally, from 0.1% w/w to 10% w/w of at least one anionic surfactant or wetting agent; optionally, 0.1% w/w to 20% w/w of at least one polymeric dispersant; optionally, from 0.5% w/w to 20% w/w of at least one stabilizer of alkaline or alkaline earth metal or salt of aluminum, ammonium, zinc and/or iron; optionally, from 0.5% w/w to 10% w/w of at least one suspension aid; optionally, from 0.1% w/w to 10% w/w of at least one biocide; optionally, from 5% w/w to 30% w/w of at least one adjuvant; optionally, at least one buffer; and water in sufficient amount to bring the total to 100% w/w; and (b) applying the formulation to the plant in an effective amount.

It is also an object of the present invention to provide a method of protecting a plant wherein said plant is selected from the group consisting of genetically modified plants, non-genetically modified plants and combinations thereof, and wherein said composition is applied to foliage of the plant, to the seed and/or fruit of the plant, at or about the root of the plant and combinations thereof.

It is also an object of the present invention to provide a method of protecting a plant wherein the seed is selected from the group consisting of corn, cotton, soybean, wheat, barley, rice, rapeseed, sugarbeet, tomato, bean, carrot, and tobacco.

It is also an object of the present invention to provide a method of preparing an agriculturally acceptable stable aqueous formulation comprising the steps of preparing an aqueous spore suspension module comprising at least one spore as but which does not contain an insecticide, pesticide or fungicide; and preparing an aqueous chemical suspension module containing said chemical but that does not contain at least one spore; and combining the spore module and the chemical module to form a stable aqueous formulation.

It is an object of the present invention to provide such a method wherein (a) the spore is a bacterial or fungal species, wherein (i) in the case of a bacterial spore it is from the Genus *Bacillus* and is at least one of *Bacillus aizawai, Bacillus cereus, Bacillus firmus, Bacillus kurstaki, Bacillus lentimorbus, Bacillus licheniformis, Bacillus megaterium, Bacillus popillae, Bacillus pumilus, Bacillus sphaericus, Bacillus subtilis*, and/or *Bacillus thuringiensis* and (ii) in the case of a fungal spore it is from the Class of Basidiomycetes, Chytridiomycetes, Deuteromycetes, Hyphochytridiomycetes, Oomycetes, Plasmodiophoromycetes, Sordariomycetes, Trichomycetes and Zygomycetes and is at least one from *Arthrobotrys superba, Arthrobotrys irregular, Beauveria bassiana, Fusarium* spp., *Hirsutella rhossiliensis, Hirsutella thompsonii, Lagenidium giganteum, Myrothecium, Nomuraea rileyi, Paecilomyces lilacinus, Trichoderma, Vericillium lecanii*, and/or *Verticillium lecanii*, (b) the chemical module exhibits a chemical loading of an active ingredient selected from the group consisting of a pesticide, a fungicide, an insecticide and combinations thereof of from 100 g/L to 750 g/L and a weight average particle size of 50% from 2 to 25 microns by the laser light scattering method; (c) the spore module has a loading of at least 20 g/L; and (d) the stable aqueous formulation exhibits a Brookfield viscosity of 150 to 3500 cps and a pH of 2.5 to 9.5.

In terms of stability in connection with the present invention, there are at least three forms of stability desired. One is physical stability, meaning the formulation stays homogenous over time, and if any separation occurs, particles easily resuspended, for example, by shaking, stirring or the like. The second is chemical stability, that the chemical component, i.e. the agriculturally active ingredient, remains active over time and does not decompose, degrade or otherwise lose its activity. And finally, the last stability desired in connection with the present invention is the viability of the biological components, e.g. that the spores of bacterial or fungal origin keep their viability over time.

A formulation of the present invention preferably includes at least one spore. A "spore" as contemplated by the present invention refers to at least one dormant (at application) but viable reproductive unit of a bacterial or fungal species. Preferably the at least one spore, once germinated, will provide the plant with a known and proven agricultural benefit.

Examples of fungal spores or conidia that are insecticidal or nematicidal or fungicidal include but not limited to the following classes: Basidiomycetes, Chytridiomycetes, Deuteromycetes, Hyphochytridiomycetes, Oomycetes, Plasmodiophoromycetes, Sordariomycetes, Trichomycetes and Zygomycetes, specifically the following fungi: *Arthrobotrys superba, Arthrobotrys irregular, Beauveria bassiana, Erynia neoaphidis, Fusarium* spp., *Hirsutella rhossffiensis, Hirsutella thompsonii, Lagenidium giganteum, Metarhiziurn anisopliae, Myrothecium, Neozygietes fresenii* (*Nowakowski*), *Nomuraea rileyi, Paecilomyces lilacinus, Pseudomonas chloroaphis, Pseudomonas* spp., *Psedozyma Flocculosa, Trichoderma*, and *Vericillium lecanii., Verticillium lecanii*, plus those endoparasitic fungi described in the book of "Nematology Advances and Perspectives, Vol. 2 (2004)", which is incorporated herein by reference in its relevant portion. Also included is a fungus genus "Esteya vermicola as described in U.S. Pat. No. 6,168,947 (incorporated by reference), as well as the "Arkansas Fungus 18' as described in U.S. Pat. No. 5,019,389 (incorporated herein by reference).

Examples of bacterial spores include but not limited to *Bacillus agri, Bacillus aizawai, Bacillus albolactis, Bacillus amyloliquefaciens, Bacillus cereus, Bacillus circulars, Bacillus coagulans, Bacillus endoparasiticus, Bacillus endorhythmos, Bacillus firmus, Bacillus kurstaki, Bacillus lacticola, Bacillus lactimorbus, Bacillus lactis, Bacillus laterosporus, Bacillus lentimorbus, Bacillus licheniformis, Bacillus macerans, Bacillus megaterium, Bacillus medusa, Bacillus metiens, Bacillus natto, Bacillus nigrificans, Bacillus popillae, Bacillus pumiliss, Bacillus pumilus, Bacillus siamensis, Bacillus sphaericus, Bacillus* spp., *Bacillus* subtillis, *Bacillus thuringiensis, Bacillus* uniflagellatus, plus those listed in the category of *Bacillus* Genus in the "Todar's Online Textbook of Bacteriology, (2009)" which is incorporated herein by reference in its relevant portion. Also included are *Photorhabdus luminescens, Xenorhabdus nematophilus, pantoea agglomerans*, and those nematicidal bacterial antagonists listed in "Nematology Advances and Perspectives, Vol. 2 (2004)." A preferred spore of the present invention is *Bacillus firmus* of strain CNCM 1-1582.

In one embodiment of the present invention, germinated spores exhibit the ability to provide a plant protection from pathogenic fungal and nematicidal species. In a particularly preferred embodiment, these spores are from the Genus *Bacillus* and in addition to the agricultural benefits they provide, they have the ability to colonize the root system of the plant to which they have been applied. The amount of spores employed is preferably about 3% w/w to about 80% w/w of the entire formulation. More preferably, the at least one spore is present in an amount of about, from 4% to 80% w/w, more preferably 5% w/w to about 75% w/w and, in some embodiments from about 10% w/w to about 60% w/w or even 10%-55% w/w.

In one embodiment, the spore is mechanically dispersed and emulsified in an aqueous medium with the aid of at least one dispersant. The dispersant, in combination with at least one surfactant (described below) stabilizes the resulting aqueous formulation by lowering the surface tension and preventing agglomeration of the spore particles.

The dispersant can be ionic or non-ionic and polymeric in structure. Particularly preferred are ionic water soluble polymers which include lignin-based dispersants such as lignin sulfonates which are water soluble polymers that carry ionic charge along the backbone chain, including ammonium, sodium, calcium and magnesium ions.

Generally, one or more of the following types of lignin-based dispersants may be used: mono-calcium salt of polymerized aryl alkylsulfonic acids, (lignosulfonate calcium salt); sodium salt of kraft lignin polymer optionally mixed with a modified sulfite lignin; ammonium lignosulfonates; lignin, alkali, and reaction product with sodium bisulfite and formaldehyde. Metal lignosulfonate salts can be prepared from the waste liquor of sulfite pulping which are then further oxidized, or desulfonated.

Metal lignosulfonate salts of the present inventive formulations can be used in an amount effective to provide adsorption of the metal lignosulfonate salt on the surfaces of certain spore particles or globules to impart a negative charge to the particle or globule. The resulting electrostatic repulsions between particles or globules then prevent heavy flocculation and aggregation.

The lignosulfonate anion moiety of the metal lignosulfonate salt is generally a product of the sulfonation of lignin. The anion may comprise polymeric molecules of weight-average molecular weight from about 2000 to 100000 g/mol (Daltons). A preferred molecular weight range is between 1000 and 80,000, more preferably from 2000 to 60000 with carbon to sulfur ratio between 9:1 to 55:1. A preferred molecular weight range is from 20000 to 30000, and a number average molecular weight of from about 1000 to about 10000 g/mol. More preferably, the molecular weight of the metal lignosulfonate salt is from 2000 g/mol to about 8000 g/mol. Examples of acceptable lignosulfonic acid salts include Borresperse® NA sodium lignosulfonate dispersant, Borresperse® CA calcium lignosulfonate dispersant, Ultrazine® NA sodium lignosulfonate dispersant and Ultrazine® CA calcium lignosulfonate dispersant. All of these dispersants are available from the Borregaard® Lignotech Company (Internet: http//:www.lignotech.com) at Borregaard P.O. Box 162 NO-1701 Sarpsborg, Norway.

Other anionic polymers or polyelectrolytes and their mixtures that may be useful in this invention include poly (acrylic acid), sodium salt; poly(styrene sulfonic acid), sodium salt; poly (2-acrylamido-2-methyl propane sulfonic acid), sodium salt; hydrolyzed polyacrylamide, sodium salt which is similar to copolymer of acrylamide and acrylic acid, sodium salt. Useful cationic polymers may include quarternary polyamines, polyethyleneimine, and poly(4-vinylpyridine). Nonionic water soluble polymers and their mixtures useful as dispersant in this invention include polyacrylamide, poly(acrylic acid), poly(methacrylic acid), poly (ethylene oxide), poly(lauryl methacrylate), poly (N-vinyl pyrrolidone), and poly(vinyl alcohol). It may be feasible that both ionic and nonionic water soluble polymer used together for synergistic dispersing action.

When utilized, the at least one dispersant is present in an amount of about 0.1% w/w to 40% w/w, preferably 0.1% w/w to about 20% w/w, and still more preferably 0.1% w/w to 15% w/w of the entire formulation. Still more preferably, the at least one dispersant is present in an amount of about 0.5% w/w to about 15% w/w and, most preferably, about 1% w/w to about 10% w/w.

In one embodiment, the formulation optionally comprises at least one surfactant. The at least one surfactant can be an emulsifier, a dispersing agent or a wetting agent, of ionic or non-ionic type or a mixture of these surfactants. The anionic or nonionic surfactant is used in an effective amount to minimize foaming of the composition upon physical mixing or dilution into water. Information about surfactants can be obtained for example from "McCutcheon's Emulsifiers & Detergents," McCutcheon Division, McCutcheon Publishing Co., 175 Rock Road, Glen Rock, N.J. 07452.

A general description of surfactants that might be used in the present invention include nonionic surfactants such as $C_8$ to $C_{18}$ alcohol alkoxylates, both linear and branched chain ethoxylates with 2 to 22 (preferably 2 to 10) EO units and with an HLB range from about 4 to 16 (preferably 2 to 12); alkyl phenol ethoxylates, mono- and di-nonyl and octyl phenol with 2 to 150 (preferably 2 to 40) EO units, HLB range from about 4 to 19 (preferably 4 to 12); fatty amine alkoxylates, e.g., tallow, oleyl, stearyl and cocoamine alkoxylates with 2 to 50 EO (preferably 2 to 20) units and HLB range from about 4 to 18 (preferably 4 to 12); alkanolamides; triglyceride alkoxylates, such as castor, rapeseed, soybean and colza oil ethoxylates with 5 to 54 (preferably 5 to 20) EO units and HLB range from about 4 to 15 (preferably 4 to 12); sorbitan ester ethoxylates with 20 to 30 EO units, HLB range from about 10 to 16 (preferably 10 to 12); ethylene oxide/propylene oxide copolymers including alkoxylated rapeseed oil with ethylene oxide and propylene oxide chains; and with an HLB range from about 1 to 18 (preferably 1 to 18); alkyl polyglycosides; fatty acid ethoxylates; fatty acid polyethylene glycols; fatty alcohol ethoxylates; di- and tristyrylphenol ethoxylates; glycerol esters; and polyol ethoxylate esters.

Other surfactants that can be utilized include, for example, phenolsulphonic or naphthalenesulphonic acid salts, polycondensates of ethylene oxide with fatty alcohols or fatty acids or fatty esters or fatty amines, substituted phenols (in particular alkylphenols or arylphenols), estersalts of sulphosuccinic acid, taurine derivatives (in particular alkyl taurates), phosphoric esters of alcohols or of polycondensates of ethylene oxide with phenols, fatty acid esters with polyols, or sulphate, sulphonate or phosphate functional derivatives of the compounds described above.

Anionic surfactants that may be used in the present inventive formulations include sulfonates, fatty alcohol ether sulfonates, fatty acid sulfonates; sulfonates, alkylbenzenesulfonates, alkyl naphthalene sulfonates, alkylaryl sulfonates, olefin sulfonates, alkylphenol ethoxylate sulfonates; phosphates, such as phosphates of fatty alcohol ethoxylate, phosphates of alkylphenol ethoxylate having 4 to 12 EO units; alkyl sulfosuccinates; carboxylates, alkylphenol ethoxylate carboxylates. In a suspoemulsion (SE) embodiment of the inventive formulation, both anionic or nonionic surfactants or mixtures thereof can be used to disperse any hydrophobic liquid phase that may be present. Typically, a mixture of anionic and nonionic surfactants, as well as oil soluble nonionic-polymers, can be used to disperse any oil phase.

Suitable oil soluble anionic surfactants include n- and iso-$C_{12}$-alkylbenzene calcium sulfonate salts and other oil soluble alkylbenzene sulfonate salts. Suitable soluble nonionic surfactants include nonylphenol ethoxylates (HLB of about 2 to 12), octylphenol ethoxylates (HLB of about 2 to 12), tributylphenol ethoxylates (HLB of about 2 to 12), alkoxylates (EO/PO) (HLB of about 2 to 12), tristyrylphenol ethoxylates (HLB of about 2 to 12), fatty alcohol ethoxylates (such as $C_9$-$C_{11}$, $C_{12}$-$C_{14}$ fatty alcohol polyglycol ether, $C_{11}$, $C_{12}$-$C_{15}$, $C_{14}$-$C_{16}$, and $C_{16}$-$C_{18}$ fatty oxo alcohol polyglycol ether, and oleyl alcohol poly glycol ether, HLB of about 2 to 12), stearyl alcohol ethoxylates, isotridecyl alcohol polyglycol ether (HLB of about 2 to 12), oleyl cetyl alcohol ethoxylates, isodecyl and tridecyl alcohol ethoxylates, sorbitan ethoxylates, sorbitan monooleate ethoxylates, sorbitan trioleate ethoxylates, sorbitan tristearate ethoxylates, sorbitan monolaurate ethoxylates, sorbitol oleate ethoxylates, fatty amine ethoxylates (coco amine and tallow amine and stearyl amine ethoxylates), and glycerol oleate ethoxylate.

In a preferred embodiment, the surfactant is a polymethyl methacrylate-polyethylene glycol graft copolymer which stabilizes the aqueous formulation and aids in moderating formulation viscosity. Any polymethyl methacrylate-polyethylene glycol graft copolymer may be used, however, the copolymer preferably has a molecular weight of 20,000 to 30,000. Particularly preferred is the polymethyl methacrylate-polyethylene glycol graft copolymer marketed as Atlox® 4913 available from ICI Specialties of Everberg, Belgium which contains approximately one third ionic polymethyl methacrylate-polyethylene oxide graft copolymer, one third water and one third propylene glycol.

When utilized, the surfactant (or sulfactants if more than one are employed) is present in the formulation in an amount of from about 0.2% w/w to about 20% w/w. More preferably, the surfactant is present in an amount from about 0.5% w/w to about 10% w/w and, most preferably, from about 1% w/w to about 8% w/w. Preferably non-ionic surfactants when utilized are present in the range of 0.2% w/w to 50% w/w, more preferably 0.2% w/w to 20% w/w and still more preferably 5% to 10% w/w. Preferably anionic surfactants when utilized are present in the range of 0.1% w/w to 25% w/w, more preferably 0.1% w/w to 10% w/w and still more preferably 0.5% w/w to 8% w/w.

Suitable adjuvants may be added to the inventive formulations to further modify the formulation performance. Adjuvants are chemicals added (often to the spray tank) and are used to enhance or modify the physical properties of a liquid spray application to improve its performance, such as spreading, foliage coverage, spray drift reduction, incompatibility, foaming reduction, evaporation, volatilization, adherence, penetration, surface tension, buffering agents, fertilizers, and others.

Adjuvant types include nonionic/anionic surfactants, organosilicones, crop oil concentrates, seed oils, methylated seed oils, phospholipids, alkyl polysaccharides, diols, water conditioners, stickers or extenders, latexes, plant penetrants, drift reduction agents, deposition agents and others. Examples include but are not limited to the lists of chemicals that may be found in Crop Protection Handbook, MeisterPro, 2006; which is incorporated herein by reference.

When utilized, adjuvants are present in the range of 5% w/w to 30% w/w.

In one embodiment, the inventive formulations include at least one biocide component. Any biocide can be added that exhibits a broad spectrum of activity against bacteria, fungi and yeasts. Preferred biocides include those that are non-volatile, stable at elevated temperatures, and exhibit low mammalian toxicity and are biodegradable in effluent systems.

Suitable biocides include at least one of 5-chloro-2-methyl-3(2H)-isothiazolone (e.g., trade name, Kathon), o-phenylphenol, sodium o-phenylphenate, cis-1-(chloroallyl)-3,5,7-triaza-1-azoniaadamantane chloride, 7-ethyl bicyclooxazolidine, 2,2-dibromo-3-nitrilopropionamide, bronopol, glutaraldehyde, copper hydroxide, cresol, dichlorophen, dipyrithione, dodidin, fenaminosulf, formaldehyde, hydrargaphen, 8-hydroxyquinoline sulfate, kasugamycin, nitrapyrin, octhilinone, oxolinic acid, oxytetracycline, probenazole, streptomycin, tecloftalam, thimerosal, polyquaternary ammonium chloride, alkylbenzyl dimethyl ammonium chloride, 2-methyl-4-isothiazolone, 2-ethyl-4-isothiazolin-3-one, 2-propyl-4-isothiazolin-3-one, 2-butyl-4-isothiazolin-3-one, 2-amyl-4-isothiazolin-3-one, 5-chloro-2-methyl-4-isothiazolin-3-one, 5-bromo-2-methyl-4-isothiazolin-3-one, 5-iodo-2-methyl-4-isothiazolin-3-one, 5-chloro-2-butyl-4-isothiazolin-3-one, 5-bromo-2-ethyl-4-isothiazolin-3-one, 5-iodo-2-amyl-4-isothiazolin-3-one, 2-n-octyl-4-isothiazolin-3-one, or 4,5-dichloro-2-n-octyl-4-isothiazolin-3-one. Particularly preferred is 1,2-benzisothiazolin-3-one comprising the biocide marketed as Proxel® GXL available from Arch Chemicals, Incorporated of Smyrna, Ga.

When utilized, the biocide is present in the formulation in an amount of from about 0.1% w/w to about 12% w/w, preferably 0.1% w/w to about 10% w/w. More preferably, the biocide is present in an amount from about 0.1% w/w to about 5% w/w, more preferably 0.2% w/w to about 5% w/w. It may also be present in the range of about 0.1% w/w to about 4% w/w and, most preferably, from about 0.3% w/w to about 3% w/w.

In one embodiment, the formulations according to the present invention include at least one insect control agent. As used herein, the term "insect control agent" broadly refers to compounds or compositions that are used as acaricides, insecticides, insecticide synergists, ixodicides, nematicides, and molluscicides. Chemical classes of insecticides include 2-dimethylaminopropane-1,3-dithiol, 2-dimethylaminopropane-1,3-dithiol analogs, amidines, arylpyrroles, avermectin, benzoylureas, carbamates, carbamoyltriazoles, cyclodienes, diacylhydrazines, dinitrophenols, fiprole, METI, neonicotinoids, non-ester pyrethroids, organochlorines, organophosphates, oxadiazines, oximes, carbamates, pyrethroids, and spinosyns.

Suitable insecticides include 1,1-bis(4-chlorophenyl)-2-ethoxyethanol, 1,1-dichloro-1-nitroethane, 1,1-dichloro-2,2-bis(4-ethylphenyl)ethane, 1,2-dichloropropane with 1,3-dichloropropene, 1-bromo-2-chloroethane, 2-(1,3-dithiolan-2-yl)phenyl dimethylcarbamate, 2-(2-butoxyethoxy)ethyl thiocyanate, 2-(4,5-dimethyl-1,3-dioxolan-2-yl)phenyl methylcarbamate, 2-(4-chloro-3,5-xylyloxy)ethanol, 2,2,2-trichloro-1-(3,4-dichlorophenyl)ethyl acetate, 2,2-dichlorovinyl 2-ethylsulfinylethyl methyl phosphate, 2,4-dichlorophenyl benzenesulfonate, 2-chlorovinyl diethyl phosphate, 2-isovalerylindan-1,3-dione, 2-methyl(prop-2-ynyl)aminophenyl methylcarbamate, 2-thiocyanatoethyl laurate, 3-bromo-1-chloroprop-1-ene, 3-methyl-1-phenylpyrazol-5-yldimethylcarbamate, 4-chlorophenyl phenyl sulf one, 4-methyl(prop-2-ynyl)amino-3,5-xylyl methylcarbamate, 4-methylnonan-5-ol with 4-methylnonan-5-one, 5,5-dimethyl-3-oxocyclohex-1-enyl dimethylcarbamate, 6-methylhept-2-en-4-ol, abamectin, acephate acequinocyl, acrinathrin, alanycarb, aldicarb, aldoxycarb, aldrin, allethrin [(1R)-isomers], allyxycarb, alpha-cypermethrin, amidithion, amidothioate, aminocarb, amiton; amiton hydrogen oxalate, amitraz, anabasine, aramite, athidathion, azadirachtin, azamethiphos, azinphos-ethyl, azinphos-methyl, azocyclotin, azothoate, barium polysulfide, Bayer 22/190, Bayer 22408, bendiocarb, benfuracarb, bensultap, benzoximate, beta-cyfluthrin, beta-cypermethrin, bifenazate, bifenthrin, binapacryl, biopermethrin, bis(2-chloroethyl) ether, bistrifluron, bromfenvinfos, bromocyclen, bromophos, bromophos-ethyl, bromopropylate, bufencarb, buprofezin, butacarb, butathiofos, butocarboxim, butonate, butoxycarboxim, cadusafos, calcium polysulfide, camphechlor, carbanolate, carbaryl, carbofuran, carbophenothion, carbosulfan, cartap hydrochloride, CGA 50 439, chinomethionat, chiorbenside, chlorbicyclen, chlordane, chlordecone, chlordimeform; chlordimeform hydrochloride, chlorethoxyfos, chiorfenapyr, chlorfenethol, chiorfenson, chlorfensuiphide, chlorfluazuron, chlormephos, chloro-benzilate, chloromebuform, chloropropylate, chlorphoxim, chiorprazophos, chlorpyrifos, chlorpyrifos-methyl, chlorthiophos, chromafenozide, cloetho-carb, clofentezine, clothianidin, codlemone, coumaphos, coumithoate, crotoxyphos, crufomate, cryolite, CS 708, cyanofenphos, cyanophos, cyanthoate, cycloprothrin, cyfluthrin, cyhalothrin, cyhexatin, cypermethrin, cyphenothrin [(1R)-trans-isomers], cyromazine, DAEP, dazomet, DCPM, DDT, decarbofuran, deltamethrin, demephion; demephion-O; demephion-S, demeton; demeton-O; demeton-S, demeton-S-methyl, demeton-S-methylsulphon, diafenthiuron, dialifos, diazinon, dicapthon, dichlorvos, dicofol, dicrotophos, dicyclanil, dieldrin, dienochlor, diethyl 5-methyl-pyrazol-3-yl phosphate, diflubenzuron, dimefox, dimethoate, dimethrin, dimethylvinphos, dimetilan, dinex; dinex-diclexine, dinobuton, dinocap, dinocton, dinopenton, dinoprop, dinosulfon, dinotefuran, dinoterbon, dioxabenzofos, dioxacarb, dioxathion, diphenyl sulfone, disulfoton, dithicrofos, DNOC, dodec-8-enyl acetate, dofenapyn, DSP, EI 1642, emam ectin benzoate, EMPC, empenthrin [(EZ)-(1R)-isomers], endosulfan, endothion, endrin, ENT 8184, EPBP, EPN, esfenvalerate, ethiofencarb, ethion, ethiprole, ethoate-methyl, ethoprophos, etofenprox, etoxazole, etrimfos, famphur, fenamiphos, fenazaflor, fenazaquin, fenbutatin oxide, fenchlorphos, fenethacarb, fenfluthrin, fenthion, fenitrothion, fenobucarb, fenothio-carb, fenoxacrim, fenoxycarb, fenpirithrin, fenpropathrin, fenpyroximate, fenson, fensulfothion, fenthion, fentrifanil, fenvalerate, fipronil, flonicamid, fluacrypyrim, flubendiamide, flubenzimine, flucofuron, flucycloxuron, flucythrinate, fluenetil, flufenerium, flufenoxuron, flufenprox, flumethrin, fluorbenside, fluvalinate, FMC 1137, fonofos, formetanate, formothion, formparanate, fosmethilan, fospirate, fosthiazate, fosthietan, furathiocarb, furethrin, gamma-cyhalo-thrin, gamma-HCH, glyodin, GY-81, halfenprox, halofenozide, heptachlor, heptenophos, hexadecyl cyclopropanecarboxylate, hexaflumuron, hexythiazox, hydramethylnon, hydroprene, hyquincarb, imidacloprid, imiprothrin, indoxacarb, iprobenfos, IPSP, isazofos, isobenzan, isodrin, isofenphos, isolane, isoprocarb, isopropyl O-(methoxyaminothio-phosphoryl)salicylate, isothioate, isoxathion, jodfenphos, kelevan, kinoprene, lambda-cyhalothrin, lepimectin, leptophos, lirimfos, lufenuron, lythidathion, m-cumenyl methylcarbamate, malathion, malonoben, mazidox, MB-599, mecarbam, mecarphon, menazon, mephosfolan, mercurous chloride, mesulfenfos, metaflumizone, metam, methacrifos, methamidophos, methanesulfonyl fluoride, methidathion, methiocarb, methocrotophos, methomyl, methoprene, methoquin-butyl, methothrin, methoxychlor, methoxyfenozide, methyl isothiocyanate, metolcarb, metoxadiazone, mevinphos, mexacarbate, milbemectin, mipafox, mirex, MNFA, monocrotophos, morphothion, naled, naphthalene, niclosamide, nicotine, nifluridide, nitenpyram, nithiazine, nitrilacarb; nitrilacarb 1:1 zinc chloride complex, nornicotine, novaluron, noviflurnuron, O,O,O'O'-tetrapropyl dithiopyrophosphate, O,O-diethyl O-4-methyl-2-oxo-2H-chromen-7-yl phosphorothioate, O,O-diethyl O-6-methyl-2-propylpyrimidin-4-yl phosphorothioate, O-2,5-dichloro-4-iodophenyl O-ethyl ethylphosphonothioate, oleic acid (fatty acids), omethoate, oxabetrinil, oxamyl, oxydemeton-methyl, oxydeprofos, oxydisulfoton, parathion, parathion-methyl, pentachlorophenol, permethrin, petroleum oils, phenkapton, phenothrin [(1R)-trans-isomer], phenthoate, phorate, phosalone, phosfolan, phosmet, phosnichlor, phosphamidon, phosphine, phoxim, phoxim-methyl, piperonyl butoxide, pirimetaphos, pirimicarb, pirimiphos-ethyl, pirimiphos-methyl, polychlorodicyciopentadiene isomers, polynactins, prallethrin, primidophos, proclonol, profenofos, promacyl, promecarb, propaphos, propargite, propetamphos, propoxur, prothidathion, prothiofos, prothoate, pymetrozine, pyraclofos, pyrafluprole, pyresmethrin, pyrethrins (pyrethrum), pyridaben, pyridalyl, pyridaphen thion, pyrimidifen, pyrimitate, pyriprole, pyriproxyfen, quinalphos, quinaiphos-methyl, quinothion, quintiofos, R-1492, RA-17, resmethrin, rotenone, RU 15525, RU 25475, S421, sabadilla, schradan, silafluofen, SN 72129, sodium fluoride, sodium hexafluorosilicate, sodium selenate, sophamide, spinosad, spirodiclofen, spiromesifen, spirotetramat (BYI8330), SSI-121, sulcofuron-sodium, sulfluramid, sulfosulfuron, sulfotep, sulfur, sulprofos, SZI-121, taroils, tazimcarb, TDE, tebufenozide, tebufenpyrad, tebupirimfos, teflubenzuron, tefluthrin, temephos, TEPP, terallethrin, terbufos, tetrachlorvinphos, tetradifon, tetramethrin, tetramethrin [(1R)-isomers], tetrasul, theta-cypermethrin, thiacloprid, thiamethoxam, thicrofos, thiocarboxime, thiocyclam, thiodicarb, thiofanox, thiometon, thionazin, thioquinox, thiosultap-sodium, tolfenpyrad, tralomethrin, transfluthrin, transpermethrin, triamiphos, triarathene, triazamate, triazophos, trichlorfon, trichloronat, trifenofos, triflumuron, trimedlure, trimethacarb, vamidothion, XMC, xylylcarb, zeta-cypermethrin, zolaprofos, and ZXI 8901.

Most preferably, the insect control agent is at least one systemic chloronicotinyl insecticide. Suitable chloronicotinyl insecticides include 1-(6-chloro-3-pyridylmethyl)-N-nitroimidazolidin-2-ylideneamine (imidacloprid), 3-(6-chloro-3-pyridylmethyl)-1,3-thiazolidin-2-ylidenecyanamide (thiacloprid), 1-(2-chloro-1,3-thiazol-5-ylmethyl)-3-methyl-2-nitroguanidine (clothianidin), nitempyran, $N^1$-[(6-chloro-3-pyridyl)methyl]-$N^2$-cyano-$N^1$-methylacetamidine (acetamiprid), 3-(2-chloro-1,3-thiazol-5-ylmethyl)-5-methyl-1,3,5-oxadiazinan-4-ylidene(nitro) amine (thiamethoxam) and 1-methyl-2-nitro-3-(tetrahydro-3-furylmethyl)guanidine (dinotefuran). In one embodiment, the biological control agent is combined with the insect control agents marketed as AERIS® and GAUCHO GRANDE®, respectively, which are commercially available from Bayer CropScience of Research Triangle Park, North Carolina (GAUCHO® and AERIS® are registered trademarks of Bayer Aktiengesellschaft, Leverkusen, Germany). Combinations of the above-listed chemicals and agents, as well as other chemicals and agents known to be effective against insects are within the scope and spirit of the present invention.

The insect control agent, when utilized, is present in an effective amount. The amount of the insect control agent employed is preferably about 1% w/w to about 99% w/w of the entire formulation. More preferably, the insect control agent is present in an amount of about 5% w/w to about 95% w/w, more preferably about 10% w/w to about 95% w/w, and, most preferably, about 10% w/w to about 90% w/w. It may also be present in the range of about 1% w/w to about 60% w/w, and more preferably about 5% w/w to about 60% w/w.

In one embodiment, the inventive formulation optionally comprises at least one water miscible solvent which is not spore swelling. Preferably, the water miscible solvent is a polar, organic solvent. Suitable water miscible organic solvents include 1,3-butylene glycol 1,2-propylene glycol monomethyl ether, 1,2-propylene glycol, 1,3-dimethyl-2-imidazolidinone, 1,4-dioxane, 2-pyrrolidone, 2-pyrrolidone, acetone, acetonitrile, aliphatic alcohol (less than C12), aliphatic carboxylic acid alkyl ester of low molecular weight, cyclohexanone, di- and triglycols, diacetone alcohol, dialkyl ketone, diethylene glycol, diethylene glycol monobutyl ether, diethylene glycol monoethyl ether, diethylene glycol monomethyl ether, diethylene glycol monopropyl ether, diglyme, dimethoxyethane, dimethoxymethane, dimethylacetamide, DMF, DMSO, ethanol, ethyl acetate, ethylene glycol monoethyl ether, ethylene glycol monomethyl ether, ethylene glycol, formamide, furfuryl alcohol, gamma-butyrolactone, glycerol, glycofurol, glycol ethers under the trade names of Cellosolve and Eastman Chemical, glycol, isopropanol, methanol, methyl ethyl ketone, methylsulfonylmethane, morpholine, N-methyl pyrrolidone, phosphoric acid esters, polyethylene glycol (low molecular weight), polyethylene glycols, polyhydroxylated alkanes, such as propylene glycol triethylene glycol, tetramethylene glyol, penta¬methylene glycol, hexa¬methylene glycol, propanol, propylene carbonate, pyrrolidine, Sulfolane, tetrahydrofuran, thiodiglycol, triethylene glycol, polyethylene glycol, plus those water miscible solvents listed in the book of "The Merck Index, 1989," and the mixtures thereof.

Generally the water miscible solvents are non-swelling for the spores, and non-swelling solvents have a density of from 0.70 to 2.5 g/mL at standard temperature and standard pressure (20° C. and 760 mm Hg respectively) and a viscosity of from 100 to 1000 cp (centipoise) as measured by a rotating plate Ostwald viscosimeter at standard temperature and pressure. Particularly preferred is propylene glycol.

The non-swelling water miscible solvent may be present in the range of about 2% w/w to about 90% w/w, preferably 5% w/w to about 90% w/w. It may also be present in the range of about 2% w/w to about 80% w/w, and is preferably about 2% w/w to about 60% w/w of the entire formulation. More preferably, the non-swelling water miscible solvent is present in an amount of about 5% w/w to about 50% w/w, preferably about 5% w/w to about 40% w/w, preferably 10% w/w to about 40% w/w and, most preferably, about 15% w/w to about 30% w/w. It may also be present in the range of about 5% w/w to about 25% w/w, preferably about 5% w/w to about 10% w/w. The hydrophobic agent may be present in the same ranges and preferably in the lower end of these ranges, preferably 2% w/w to 15% w/w. Water may be used in any event in sufficient amount to bring the total formulation weight to 100%.

In one embodiment, the inventive formulation optionally comprises at least one aqueous emulsion of a hydrophobic agent (HA) preferably containing an oil soluble emulsifier. Preferably, the HA comprises a nonpolar liquid, such as severely hydrogenated naphthenic distaillate as disclosed in U.S. Pat. No. 4,487,687 and/or (CAS Nos. 64742-52-5 & 64742-53-6) and hydrogenated-vegetable and plant sourced oils such as almond oil, canola oil, coconut oil, corn oil, cottonseed oil, flaxseed oil, grape seed oil, jojoba oil, linseed oil, mustard oil, olive oil, palm oil, peanut oil, rapeseed oil, rice bran oil, safflower oil, sesame oil, soybean oil, sunflower oil, and walnut oil and their mixtures.

When utilized, the hydrophobic agent may be present in the range of about 2% w/w to about 90% w/w, preferably about 3% w/w to about 90% w/w, preferably 5% to about 90% w/w and still more preferably about 5% to about 50% w/w.

In one embodiment, the formulation comprises one or more other fungicidal active materials chosen from acibenzolar-S-methyl, azoxystrobin, benalaxyl, benalaxyl-M, benomyl, benthiavalicarb-isopropyl, bitertanol, blasticidin-S, boscalid, bromuconazole, captafol, captan, carbendazim, carboxin, carpropamide, chlorothalonil, fungicidal compositions based on copper, derivatives of copper such as copper hydroxide and copper oxychloride, cyazofamide, cylfufenamid, cymoxanil, cyproconazole, cyprodinil, dichloran, diclocymet, diethofencarb, difenoconazole, diflumetorim, dimethomorph, diniconazole, discostrobin, dodemorph, dodine, edifenphos, epoxyconazole, ethaboxam, ethirimol, famoxadone, fenamidone, fenarimol, fenbuconazole, fenhexamide, fenpiclonil, fenpropidine, fenpropimorph, ferimzone, fluazinam, fludioxonil, flumetover, fluopicolide, fluoxastrobin, fluquinconazole, flusilazole, flusulphamide, flutolanil, flutriafol, folpel, fosetyl-Al, furalaxyl, furametpyr, guazatine, hexaconazole, hymexazol, imazalil, ipconazole, iprobenphos, iprodione, iprovalicarb, isoprothiolane, kasugamycin, kresoxim-methyl, mancozeb, mandipropamid, maneb, mefenoxam, mepanipyrim, metalaxyl and their enantiomeric forms such as metalaxyl-M, metconazole, metiram-zinc, metominostrobin, oxadixyl, metrafenone, orysastrobin, pefurazoate, penconazole, pencycuron, penthiopyrad, phtalide, picoxystrobin, probenazole, prochloraz, procymidone, propamocarb, propiconazole, proquinazid, prothioconazole, pyraclostrobin, pyrimethanil, pyroquilon, quinoxyfen, silthiofam, simeconazole, spiroxamine, tebuconazole, tetraconazole, thiabendazole, thifluzamide, thiophanate, thiophanate-methyl, thiram, tolyfluanid, triadimefon, triadimenol, tricyclazole, tridemorph, trifloxystrobin, triticonazole, derivatives of valinamide such as for example, iprovalicarb, vinclozolin, zineb and zoxamide.

When present the fungicidal active materials may be present in the range of about 1% w/w to about 60% w/w, preferably about 5% w/w to about 60% w/w.

The inventive formulations may further comprise one or more additives such as at least one suspension aid, an adjuvant, an antifoaming agent, and a colorant. Synergists may be introduced to increase the overall effectiveness of any insecticide. Suitable synergists include piperonyl butoxide, sesamax, dodecyl imidazole, safroxan, or combinations thereof. Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be added to the present formulations. Other suitable additives include mineral and vegetable oils or dyes. It is possible to use colorants such as inorganic pigments, such as, for example: iron oxides, titanium oxides, Prussian blue; organic dyestuffs, such as those of the alizarin, azo or metal phthalocyanin type; or of trace elements such as iron, manganese, boron, copper, cobalt, molybdenum or zinc salts.

The inventive formulations can also contain acaricides, nematicides, anti-helminths or anti-coccidoses, bactericides, attractant or repellent agents or pheromones for arthropods or vertebrates, deodorizers, or flavorings.

The inventive formulations can further comprise disinfectants, repellents and growth regulators, agents capable of protecting seeds from the harmful effects of selective herbicides such as activated carbon, nutrients (fertilizers), other agents capable of improving the germination and quality of the products or a combination thereof.

Preferably metal salts, comprising of chemically stable compounds of cations and anions either mono- or polyatomic in structure, are employed as stabilizers, which are believed to aid in the inhibition of spore germination. The cations include but not limited to aluminium, ammonium, calcium, copper, iron, lithium, magnesium, potassium, sodium, and zinc. The corresponding anions, include but not limited to acetates, aluminates, arsenates, benzoate, borates, bromides, carbonates, chlorates, chlorides, chlorites, chromates, citrates, condensed phosphates, cyanates, cyanides, dichromates, dihydrogen phosphates, dihydrogen phosphates, fluorides, formates, hydrogen carbonates (or bicarbonates), hydrogen phosphate, hydrogen phosphites, hydrogen sulfites (or bisulfites), hydroxides, hypochlorites, hypophosphites, iodides, lactates, nitrates, nitrites, orthoborates, orthophosphates, oxalates, perchlorates, phosphates, phosphides, phosphonates, pyrophosphates, salicylates, silicates, sulfamates, sulfates, sulfides, sulfites, tartrates, thiocyanates, thiosulfates, and valerates. In practicing the present invention, salts of the above cations and anions in various chemical combinations are usually stable and soluble in the aqueous solvent liquid medium.

The at least one stabilizer is preferably present in an amount of about 0.5% w/w to about 30% w/w, preferably 0.5% w/w to about 20% w/w of the entire formulation. More preferably, the stabilizer is present in an amount of about 2% w/w to about 15% w/w and, most preferably, about 4% w/w to about 10% w/w.

Buffers can be added to regulate pH and include organic acids, such as citric acid and ascorbic acid, as well as inorganic acids such as hydrochloric acid or sulfuric acid. The amount of buffer added is dependent upon the preferred pH which, in turn, depends on the stability and dormancy of the bacterial spore utilized in the inventive formulation. Preservatives can also be added and can include formaldehydes or formaldehyde-releasing agents and derivatives of benzoic acid, such as p-hydroxybenzoic acid.

When utilized, buffers may be present in the range of about 0.1% w/w to about 3% w/w In one embodiment, the formulation comprises a stabilizing amount of at least one suspension aid. The suspension aid can be added to help maintain the at least one spore in suspension thus improving the spore's resistance to settle statically and flow under shear or rheological shear-thinning. Suitable suspension aids include but not limited to water soluble polymers such as 3-butoxy-2-hydroxypropylhydroxyethylcellulose, acrylamide homo- and copolymers, acrylic acid homo- and copolymer, alginates, carboxymethylcellulose (sodium and other salts), carboxymethylhydroxyethylcellulose, carboxy-vinyl copolymers, cellulose, guar gum, gum arabic; hydrophobically modified hydroxyethylcellulose, hydroxyethylcellulose, hydroxypropyl guar, hydroxypropyl methylcellulose, hydroxypropylcellulose, natural gums and their derivatives, partially and fully hydrolyzed polyvinyl alcohols, partially neutralized polyacrylic acid, polyalkylene glycol, polysaccharide gums, polyvinylpyrrolidone and derivatives, sodium carboxymethylcellulose, starch and its derivatives, vinylpyrrolidone homo- and copolymers, water-soluble cellulose ethers, xanthan gum, and the mixtures thereof. Another suspension aid used in the present invention include silica powder prepared by precipitating water glass (sodium silicate) with sulfuric acid, which is then dried and sold as a fine powder. The silica powder provides a rheology control and aid in suspension by preventing particle settling. Still another suspension aid material is fumed alumina. Alulmina or aluminium oxide is an amphoteric oxide of aluminium with the chemical formula $AL_2O_3$. Fumed alumina is made of primary particles which sinter together to form aggregates. These alumina aggregates have a chain-like structure and an average diameter of 150 nm (for primary particle size of 20 nm) It also provides a rheology control and lubrication for the spore suspension concentrate. Optionally clays may also be used in the present invention. Such clays include bentonite, laponites, kaolinite, dickite, and nacrite, with the general formula of $Al_2Si_2O_5(OH)_4$; pyrophylite, talc, vermiculite, sauconite, saponte, nontronite, and montmorillonite with the general chemical formula (Ca, Na, H) (Al, Mg, Fe, Zn)$_2$(Si, Al)$_4O_{10}(OH)_2 \cdot xH_2O$; attapulgite with the general chemical formula $Mg_5Si_8O_{20}(HO)_2(OH_2)_4 \cdot 4H_2O$; and illite with the general formula (K, H) $Al_2(Si, Al)_4O_{10}(OH)_2 \cdot xH_2O$, and organically modified montmorillonite clays. Preferably, the suspension aid is xanthan gum, hydroxypropyl cellulose, ethyl cellulose, vinyl pyrrolidone homo- and co-polymers, polyacrylic acid, sodium polyacrylate, hydroxyethyl cellulose, carboxyl methyl cellulose, guar gum, starch, derivitized guar and polyacrylamide, attapulgite, montmorillonite, organically modified montmorillonite clays, alumina, or precipitated silica or the mixture thereof. Preferably, the suspension aid is xanthan gum, clay, alumina, or precipitated silica-based suspension aids such as those available from PPG Industries of Pittsburgh, Pa. and marketed under the Hi-Sil® trademark or a combination thereof.

When utilized, the suspension aid may be present in the range of about 0.5% w/w to about 25% w/w, preferably 0.5% w/w to about 10% w/w and more preferably 0.5% w/w to about 8% w/w.

The present inventive formulations are preferably prepared in a modular manner. In a preferred embodiment, at least one chemical module and at least one spore module are prepared separately and then combined to form the final, stable, low to medium viscosity spore-containing aqueous formulation. The chemical module is prepared by blending the chemical insecticides and/or fungicides with water, solvent, stabilizer, buffer, surfactant, dispersant, biocide and other additive components (i.e., non-spore components) together, followed by wet milling according to suspension particle size reduction methods known by one of ordinary skill. The chemical module is typically concentrated resulting in a highly loaded suspension, and the resultant concentration of the chemical module is maintained in range of about 100 g/l to about 750 g/l, preferably about 500 g/L to about 700 g/L depending on the nature of the chemical components utilized. The chemical module of the present invention preferably exhibits a weight average particle size of 50% from 2 to 50, preferably 2 to 40, preferably 2 to 25, preferably 2 to 20, preferably 5 to 20 microns by the standard light scattering method, and still more preferably from 5 to 15 microns.

The spore module preferably comprises a high spore concentration of at least about 20 g/L and preferably <400 g/L. Preferably, the spore module is either added directly to the chemical module, or formulated separately as a suspension prior to the addition. In a preferred embodiment, the spore module does not require grinding thus remaining in particulate form. The spore module is then mixed with the chemical module under mild agitation resulting in a low to medium viscosity profile which is particularly advantageous to both the seed treater and farmer. Preferably, the spore module acts a thickening agent or viscosifier upon being mixed with the chemical module. In a preferred embodiment, the viscosity is from 150 to 3500 cps, preferably 150 to 2000 cps, preferably 250 to 1800 cps measured by the Brookfield method. It may also be present in the range of from 150 to 1500 cps. The pH of the stable aqueous formulation is preferably in the range of about 2.5 to 9.5. Note that in some embodiments of the present invention, the physical properties listed herein for the chemical module and/or spore module can relate to desired properties of the aqueous liquid formulation that includes at least one spore in a solvent, with or without additional component(s).

While an aqueous liquid formulation is most preferred, customary formulations may be prepared from the resulting formulation which include solutions, emulsions, wettable powders, suspensions, powders, dusting agents, pastes, soluble powders, granules, suspension-emulsion concentrates, natural and synthetic materials impregnated with active compound, and very fine capsules in polymeric substances.

The present invention also provides methods of treating a plant. The inventive formulations can be applied to the crop to be treated by means of a suitable device, such as a spraying device, but also commercial concentrated compositions which need to be diluted before they are applied onto the crop. In a preferred embodiment, the inventive formulations can be utilized in an effective amount on the soil (i.e., in furrow), to a portion of the plant (i.e., foliar) or on the seed before planting (i.e., seed coating) and/or to fruit of a plant. In a powder-based application, the inventive formulation can be used as an aqueous component at the time of use.

In one embodiment, the inventive formulations can be used for combating the phytopathogenic diseases of crops by applying an effective amount of the inventive formulation onto the plants or onto the medium in which they are growing. For such a method, the active materials are generally applied onto the target area at an effective dose of between about 20 g and about 200 g of active materials in total per hectare of area treated. Under ideal conditions, depending on the nature of the disease to be treated, a lower dose may offer adequate protection. Conversely, poor climatic conditions, resistance or other factors may require higher doses of active materials.

In a particularly preferred embodiment, the inventive formulation is utilized as a seed treatment. According to the present invention, the seeds are substantially uniformly coated with one or more layers of the formulations disclosed herein using conventional methods of mixing, spraying or a combination thereof through the use of treatment application equipment that is specifically designed and manufactured to accurately, safely, and efficiently apply seed treatment products to seeds. Such equipment uses various types of coating technology such as rotary coaters, drum coaters, fluidized bed techniques, spouted beds, rotary mists or a combination thereof. Liquid seed treatments such as those of the present invention can be applied via either a spinning "atomizer" disk or a spray nozzle which evenly distributes the seed treatment onto the seed as it moves though the spray pattern. Preferably, the seed is then mixed or tumbled for an additional period of time to achieve additional treatment distribution and dried.

The seeds may be coated via a batch or continuous coating process. In a continuous coating embodiment, continuous flow equipment simultaneously meters both the seed flow and the seed treatment products. A slide gate, cone and orifice, seed wheel, or weighing device (belt or diverter) regulates seed flow. Once the seed flow rate through treating equipment is determined, the flow rate of the seed treatment is calibrated to the seed flow rate in order to deliver the desired dose to the seed as it flows through the seed treating equipment. Additionally, a computer system may monitor the seed input to the coating machine, thereby maintaining a constant flow of the appropriate amount of seed.

In a batch coating embodiment, batch treating equipment weighs out a prescribed amount of seed and places the seed into a closed treating chamber or bowl where the corresponding dose of seed treatment is then applied. This batch is then dumped out of the treating chamber in preparation for the treatment of the next batch. With computer control systems, this batch process is automated enabling it to continuously repeat the batch treating process.

In either embodiment, the seed coating machinery can optionally be operated by a programmable logic controller that allows various equipment to be started and stopped without employee intervention. The components of this system are commercially available through several sources such as Gustafson Equipment of Shakopee, Minn.

A variety of additives known to one of ordinary skill such as adhesives or binders may be added to the seed treatment formulation. Suitable binders include those composed preferably of an adhesive polymer that may be natural or synthetic and is without phytotoxic effect on the seed to be coated. At least one suitable colorant may also be added. Any of a variety of colorants may be employed, including organic chromophores classified as nitroso, nitro, azo, including monoazo, bisazo and polyazo, diphenylmethane, triarylmethane, xanthene, methine, acridine, thiazole, thiazine, indamine, indophenol, azine, oxazine, anthraquinone and phthalocyanine. Other additives that can be added include trace nutrients such as salts of iron, manganese, boron, copper, cobalt, molybdenum and zinc. A polymer or other dust control agent can be applied to retain the treatment on the seed surface.

In one embodiment, the inventive seed coating formulation can contain at least one filler which is an organic or inorganic, natural or synthetic component with which the active components are combined to facilitate its application onto the seed. Preferably, the filler is an inert solid such as clays, natural or synthetic silicates, silica, resins, waxes, solid fertilizers (for example ammonium salts), natural soil minerals, such as kaolins, clays, talc, lime, quartz, attapulgite, montmorillonite, bentonite or diatomaceous earths, or synthetic minerals, such as silica, alumina or silicates, in particular aluminium or magnesium silicates.

Any crop seed can be treated in accordance with the invention. This includes genetically modified crops, non-genetically modified crops and combinations thereof. Crop seeds that can be treated in accordance with the present invention include such crops as fruits and vegetables. In one embodiment, the crop seeds that may be coated include soybean, wheat, barley, rice, rapeseed, sugarbeet, tomato, bean, carrot, tobacco and some flower seeds. Preferably, cotton or corn seeds are coated with the present formulations.

Having disclosed the subject matter of the present invention, it should be apparent that many modifications, substitutions and variations of the present invention are possible in light thereof. It is to be understood that the present invention can be practiced other than as specifically described. Such modifications, substitutions and variations are intended to be within the scope of the present application. As used in the following claims, articles such as "a", "the" and so on can connote the singular or the plural of the object following.

EXAMPLE 1

A stand alone liquid spore suspension (A) of this invention was as prepared as follows: fifty five grams of a *Bacillus firmus* powder of strain CNCM 1-1582 were with a strength of $1\times1^{11}$ (cfu/g) mixed with solvents and solutions, in the following order, propylene glycol (50 g), saturated potassium chloride solution (24.75 g), and water (106 g), followed by Atlox 4913 a surfactant available from Croda Corp. of New Castle, Del. (7.5 g), Borresperse NA (1.5 g) a dispersant available from Lignotech USA, Inc., of Rothschild, Wis., Agrimer 15 (5 g) a dispersant available from ISP Corp. of Wayne, N.J. and Proxel GXL (0.25 g) a biocide available from Arch Chemical of Norwalk, Conn. The sample was mixed thoroughly until homogeous. A similar *B. firmus* suspension (B) was prepared by adding Essential fertilizer solution as disclosed in U.S. Pat. No. 6,471,741 to CNCM 1-1582 spore of equivalent weight to yield a 22% spore suspension. Viscosities of both samples were measured and compared, Sample A had a viscosity of 270 cps while Sample B had 1280 cps by Brookfield LVT viscometry. Usually lower viscosities are preferred. Also it was found that sample B, the spore in the Essential medium, exhibited a lot of gassing, suggesting undesirable spore germination in the jar.

Sample A was further evaluated in standard seed treatment formulations involving Clothianidin pesticide, Poncho 250 and Poncho 1250, both available from Bayer CropScience LP of Research Triangle Park, North Carolina. Plantability test of treated corn seeds with and without the *B. firmus* spores showed no statistical difference (average of 99% with and without *B firmus* spores). The plantability of treated seeds is defined as percentage of singulation when the seeds coated with spore, polymer, and pesticides flow through seed application equipment, such as John Deer planter units running at 80° F. and 70-80% humidity.

EXAMPLE 2

A stand alone liquid spore suspension (C) of this invention was as prepared as follows: a *Bacillus firmus* powder of strain CNCM 1-1582 with a strength of $1\times1^{11}$(cfu/g) (6.6 g) was mixed with a hydrophobic agent first, Tufflo Oil (0.33 g) a hydrophobic agent available from Nynas USA Inc., of Houston, Tex., followed by Aerosil R972 (0.06 g) a silica suspension aid available from Evonik Corp of Parsippany, N.J., solvent propylene glycol (7.8 g), Emulsogen EL360 (0.3 g) a surfactant available from Clariant Corp., of Charlotte, N.C., water (14.7 g), Van Talc 6H (0.03 g) a suspension aid available from R. T. Vanderbilt of Norwalk, Conn., Borresperse NA (0.15) and Proxel GXL (0.03 g). The sample was mixed thoroughly until homogenous. The resultant spore suspension has a density of 1.109 g/ml and viscosity of 143 mPa·s by an Anton Paar SVM 3000 viscometer at 20 C.

EXAMPLE 3

The chemical module of a spore chemical combo was prepared as follows: by mixing and wet milling a mixture of Clothianidin 57%, water 31.4%, glycerin 4%, EO-PO nonionic surfactant (HLB=13-15) 3%, Morwet D425 1.2% a wetting agent available from Akzo Nobel of Chicago, Ill., Atlox 4913, 1.2%, Agrimer 15, 1%, and suspension aid, 0.9%, Proxel GXL, 0.1%, and silicone antifoamer, 0.2%. The particle size was controlled to about 3 to 4 microns at 50% population by laser light diffraction technique. Viscosity of the sample was 235 cps by Brookfield LVT vicometry, and the final Clothianidin concentration of the suspension was 728 g/l.

Preparation of the spore module of the combo formulation followed that of Example 1, *Bacillus firmus* powder of strain CNCM I-1582 11%, Agnique PG 8107U 0.5% a surfactant available from Cognis Corp., of Cincinnati, Ohio, water 23%, and saturated potassium chloride solution 22.5%. After mixing the spore module till uniformity, the above chemical module was added next to the spore module at a ratio of 43 to 57 w/w, respectively to complete the combo formulation. It was found that both modules could not be stand-alone for lacking the necessary commercial qualities, however, the final combo demonstrated good chemical, physical and biological stability.

EXAMPLE 4

As in Example 2, a chemical module consisting of two chemicals, one insecticide (Imidacloprid) and one nematicide (Thiodicarb), was prepared as follows: Imidacloprid 33%, Thiodicarb 24%, EO-PO nonionic surfactant (HLB=13-15) 3%, Morwet D425 1%, Atlox 4913, 1%, citric acid 0.1%, glycerin 8%, and Proxel GXL, 0.1%, silicone antifoamer, 0.2%, and water 29.6%. The batch was wet-milled to a particle size of 9.4 micron (50% volume average) and the resultant pH was 3.5; its Brookfield viscosity, 160 cps.

The spore module consisted of *Bacillus firmus* powder of strain CNCM I-1582 8.5%, Atlox 4913 1.2%, Borresperse NA 0.3%, glycerin 5.5%, Proxel GXL 0.2% and water 13.3% to make up the 29% (w/w) portion of the final combo formulation. The 71% (w/w) balance was filled by the above chemical module. The combo formulation had a particles size volume average of 14.4 microns, pH of 7.9, and a viscosity profile of 1160 cps by Brookfield LVT model. In terms of loading, the combo contained 291 g/l Imidacloprid, 203 g/l Thiodicarb, and *B. firmus* spore, 105 g/l. It also demonstrated a bio-viability of a minimum of 6 months at room temperature.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. An agriculturally acceptable stable aqueous formula comprising
   (a) a *Bacillus firmus* I-1582 spores in an amount of 10% w/w to 55% w/w,
   (b) glycerin in an amount of 5% w/w to 50% w/w,
   (c) water,
   (d) a stabilizer in an amount of 0.5% w/w to 20% w/w, comprising a chemical salt selected from the group consisting of sodium sulfate, sodium chloride, potassium chloride and zinc sulfate; and
   (e) clothianidin.

2. The formulation of claim 1 further comprising one or more of a surfactant, a dispersant, a suspension aid, and a biocide.

3. The formulation of claim 2, wherein
   (a) the surfactant is selected from the group consisting of a nonionic surfactant, an anionic surfactant and combinations thereof;
   (b) the dispersant is selected from the group consisting of an ionic water soluble polymer, an anionic water soluble polymer and combinations thereof,
   wherein
      i) the ionic water soluble polymer is selected from the group consisting of lignin sulfonate dispersant, polyacrylate, or a sodium salt of said polyacrylate or combination thereof; and
      ii) the nonionic water soluble polymer is a vinyl pyrrolidone homopolymer or copolymer, or poly(vinyl alcohol) and/or poly(ethylene oxide), or mixtures thereof;
   (c) the suspension aid is selected from the group consisting of xanthan gum, hydroxypropyl cellulose, ethyl cellulose, vinyl pyrrolidone homo- and co-polymers, polyacrylic acid, sodium polyacrylate, hydroxyethyl cellulose, carboxy methyl cellulose, guar gum, starch, derivatized guar, derivatized polyacrylamide, attapulgite, montmorillonite, organically modified montmorillonite clays, alumina, and precipitated silica; and
   (d) the biocide is selected from the group consisting of 5-chloro-2-methyl-3(2H)isothiazolone, o-phenylphenol, sodium o-phenylphenate, cis-1-(chloroallyl)-3,5,7-triaza-1-zoniaadamantane chloride, 7-ethyl bicyclooxazolicline, 2,2-dibromo-3-nitrilopropionamide, bronopol, glutaraldehyde, copper hydroxide, cresol, dichlorophen, dipyrithione, dodidin, fenaminosulf, formaldehyde, hydrargaphen, 8-hydroxyquinoline sulfate, kasugamycin, nitrapyrin, octhilinone, oxolinic acid, oxytetracycline, probenazole, streptomycin, tecloftalam, thimerosal, polyquatemary ammonium chloride, alkylbenzyl dimethyl ammonium chloride, 2-methyl-4-isothiazoione, 2-ethyl-4-isothiazolin-3-one, 2-propyl-4-isothiazolin-3-one, 2-butyl-4-isothiazolin-3-one, 2-amyl-4-isothiazolin-3-one, 5-chloro-2-methyl-4-isothiazolin-3-one, 5-bromo-2-methyl-4-isothiazolin-3-one, 5-iodo-2-methyl-4-isothiazolin-3-one, 5-chloro-2-butyl-4-isothiazolin-3-one, 5-bromo-2-ethyl-4-isothiazolin-3-one, 5-iodo-2-amyl-4-isothiazolin-3-one, 2-n-octyl-4-isothiazolin-3-one, 4,5-dichloro-2-n-octyl-4-isothiazolin-3-one, and 1,2-benzisothiazolin-3-one.

4. The formulation of claim 3 comprising one or more of the following:
   a) from 0.2% w/w to 20% w/w of said nonionic surfactant and from 0.1% w/w to 10% w/w of said anionic surfactant;
   b) from 0.1% w/w to 20% w/w of said dispersant;
   c) from 0.5% w/w to 10% w/w of said suspension aid;
   d) from 0.1% w/w to 10% w/w of said biocide; and
   e) water in a sufficient amount to bring to 100% w/w.

5. The formulation of claim 1 that exhibits a viscosity between 150 to 3500 cps by Brookfield viscometry and a pH of about 2.5 to 9.5.

6. The formulation of claim 1, wherein the stabilizer is sodium chloride.

7. The formulation of claim 1 wherein the glycerin is in an amount of 5-10% w/w, and the stabilizer is in an amount of 2-15% w/w.

8. The formulation of claim 1, further comprising from 0.2% w/w to 20% w/w of a nonionic surfactant.

9. The formulation of claim 1, further comprising from 0.1% w/w to 10% w/w of an anionic surfactant.

10. The formulation of claim 1, further comprising from 0.2% w/w to 20% w/w of a nonionic surfactant and from 0.1% w/w to 10% w/w of an anionic surfactant.

11. The formulation of claim 1, further comprising from 0.1% w/w to 20% w/w of a dispersant, wherein said dispersant is an ionic water soluble polymer selected from the group consisting of lignin sulfonate dispersant, polyacrylate, or a sodium salt of said polyacrylate or combination thereof.

12. The formulation of claim 1, further comprising from 0.1% w/w to 20% w/w of a dispersant, wherein said dispersant is a nonionic water soluble polymer which is a vinyl pyrrolidone homopolymer or copolymer, or poly(vinyl alcohol) or poly(ethylene oxide), or a mixture thereof.

13. The formulation of claim 1, further comprising from 0.1% w/w to 20% w/w of a dispersant, wherein said dispersant is a combination of:
   (i) an ionic water soluble polymer selected from the group consisting of lignin sulfonate dispersant, polyacrylate, or a sodium salt of said polyacrylate or combination thereof, and
   (ii) a nonionic water soluble polymer which is a vinyl pyrrolidone homopolymer or copolymer, or poly(vinyl alcohol) and/or poly(ethylene oxide), or a mixture thereof.

14. The formulation of claim 1, further comprising from 0.5% w/w to 10% w/w of a suspension aid selected from the group consisting of:
   xanthan gum, hydroxypropyl cellulose, ethyl cellulose, vinyl pyrrolidone homo- and co-polymers, polyacrylic acid, sodium polyacrylate, hydroxyethyl cellulose, carboxy methyl cellulose, guar gum, starch, derivatized guar, derivatized polyacrylamide, attapulgite, montmorillonite, organically modified montmorillonite clays, alumina, and precipitated silica.

15. The formulation of claim 1, further comprising from 0.1% w/w to 10% w/w of a biocide selected from the group consisting of:
   5-chloro-2-methyl-3(2H)isothiazolone, o-phenylphenol, sodium o-phenylphenate, cis-1-(chloroallyl)-3,5,7-triaza-1-zoniaadamantane chloride, 7-ethyl bicyclooxazolicline, 2,2-dibromo-3-nitrilopropionamide, bronopol, glutaraldehyde, copper hydroxide, cresol, dichlorophen, dipyrithione, dodidin, fenaminosulf, formaldehyde, hydrargaphen, 8-hydroxyquinoline sulfate, kasugamycin, nitrapyrin, octhilinone, oxolinic acid, oxytetracycline, probenazole, streptomycin, tecloftalam, thimerosal, polyquatemary ammonium chloride, alkylbenzyl dimethyl ammonium chloride, 2-methyl-4-isothiazoione, 2-ethyl-4-isothiazolin-3-one, 2-propyl-4-isothiazolin-3-one, 2-butyl-4-isothiazolin-3-one, 2-amyl-4-isothiazolin-3-one, 5-chloro-2-methyl-4-isothiazolin-3-one, 5-bromo-2-methyl-4-isothiazolin-3-one, 5-iodo-2-methyl-4-isothiazolin-3-one, 5-chloro-2-butyl-4-isothiazolin-3-one, 5-bromo-2-ethyl-4-isothiazolin-3-one, 5-iodo-2-amyl-4-isothiazolin-3-one, 2-n-octyl-4-isothiazolin-3-one, 4,5-dichloro-2-n-octyl-4-isothiazolin-3-one, and 1,2-benzisothiazolin-3-one.

16. The formulation of claim 1, further comprising:
   a) from 0.2% w/w to 20% w/w of a nonionic surfactant and from 0.1% w/w to 10% w/w of an anionic surfactant;
   b) from 0.1% w/w to 20% w/w of a dispersant, wherein said dispersant is a combination of:
      (i) an ionic water soluble polymer selected from the group consisting of lignin sulfonate dispersant, polyacrylate, or a sodium salt of said polyacrylate or combination thereof, and
      (ii) a nonionic water soluble polymer which is a vinyl pyrrolidone homopolymer or copolymer, or poly(vinyl alcohol) and/or poly(ethylene oxide), or a mixture thereof;
   c) from 0.5% w/w to 10% w/w of a suspension aid selected from the group consisting of xanthan gum, hydroxypropyl cellulose, ethyl cellulose, vinyl pyrrolidone homo- and co-polymers, polyacrylic acid, sodium polyacrylate, hydroxyethyl cellulose, carboxy methyl cellulose, guar gum, starch, derivatized guar, derivatized polyacrylamide, attapulgite, montmorillonite, organically modified montmorillonite clays, alumina, and precipitated silica;
   d) from 0.1% w/w to 10% w/w of a biocide selected from the group consisting of 5-chloro-2-methyl-3(2H)isothiazolone, o-phenylphenol, sodium o-phenylphenate, cis-1-(chloroallyl)-3,5,7-triaza-1-zoniaadamantane chloride, 7-ethyl bicyclooxazolicline, 2,2-dibromo-3-nitrilopropionamide, bronopol, glutaraldehyde, copper hydroxide, cresol, dichlorophen, dipyrithione, dodidin, fenaminosulf, formaldehyde, hydrargaphen, 8-hydroxyquinoline sulfate, kasugamycin, nitrapyrin, octhilinone, oxolinic acid, oxytetracycline, probenazole, streptomycin, tecloftalam, thimerosal, polyquatemary ammonium chloride, alkylbenzyl dimethyl ammonium chloride, 2-methyl-4-isothiazoione, 2-ethyl-4-isothiazolin-3-one, 2-propyl-4-isothiazolin-3-one, 2-butyl-4-isothiazolin-3-one, 2-amyl-4-isothiazolin-3-one, 5-chloro-2-methyl-4-isothiazolin-3-one, 5-bromo-2-methyl-4-isothiazolin-3-one, 5-iodo-2-methyl-4-isothiazolin-3-one, 5-chloro-2-butyl-4-isothiazolin-3-one, 5-bromo-2-ethyl-4-isothiazolin-3-one, 5-iodo-2-amyl-4-isothiazolin-3-one, 2-n-octyl-4-isothiazolin-3-one, 4,5-dichloro-2-n-octyl-4-isothiazolin-3-one, and 1,2-benzisothiazolin-3-one; and
   e) water in a sufficient amount to bring to 100% w/w.

17. The formulation of claim 1, wherein the (a) *Bacillus firmus* 1-1582 spores and (e) clothianidin are present at a ratio (a):(e) of from 2.5:1 to 10:1.

18. A method of protecting a plant comprising applying the formulation of claim 1 to the plant in an effective amount.

19. The method of claim 18 wherein said plant is selected from the group consisting of genetically modified plants, non-genetically modified plants and combinations thereof, and wherein said composition is applied to foliage of the plant, to the seed and/or fruit of the plant, at or about the root of the plant and combinations thereof.

20. The method of claim 18 or 19, wherein the formulation is applied to a seed selected from the group consisting of corn, cotton, soybean, wheat, barley, rice, rapeseed, sugarbeet, tomato, bean, carrot, and tobacco.

21. The method of claim 18, wherein the formulation comprises *bacillus firmus* spores in an amount of 3% w/w to 80% w/w;
   at least one water miscible solvent and/or an aqueous emulsion of a hydrophobic agent in an amount of 5% w/w to 50% w/w,
   from 1% w/w to 60% w/w of clothianidin,
   optionally, from 0.2% w/w to 20% w/w of a nonionic surfactant;
   optionally, from 0.1% w/w to 10% w/w of an anionic surfactant or wetting agent;

optionally, 0.1% w/w to 20% w/w of a polymeric dispersant;

optionally, from 0.5% w/w to 20% w/w of a stabilizer of alkaline or alkaline earth metal or salt of aluminum, ammonium, zinc and/or iron;

optionally, from 0.5% w/w to 10% w/w of a suspension aid;

optionally, from 0.1% w/w to 10% w/w of a biocide;

optionally, from 5% w/w to 30% w/w of an adjuvant;

optionally, a buffer; and water in sufficient amount to bring the total to 100% w/w.

22. A method of preparing the agriculturally acceptable stable aqueous formulation of claim 2 comprising:

preparing an aqueous spore suspension module comprising spores as claimed in claim 1 which does not contain an insecticide, pesticide or fungicide;

preparing an aqueous chemical suspension module containing said clothianidin but that does not contain a spore; and combining the spore module and the chemical module to form a stable aqueous formulation.

23. The method of claim 22, wherein a) the spores are *Bacillus firmus* b) the chemical module exhibits a chemical loading of clothianidin from 100 g/L to 750 g/L and a weight average particle size of 50% from 2 to 25 microns by the laser light scattering method;

c) the spore module has a loading of at least 20 g/L; and d) the stable aqueous formulation exhibits a Brookfield viscosity of 150 to 3500 cps and a pH of 2.5 to 9.5.

* * * * *